United States Patent
Fischer et al.

(10) Patent No.: US 9,359,419 B2
(45) Date of Patent: Jun. 7, 2016

(54) TREATMENT OF VASCULAR COMPLICATIONS OF DIABETES

(75) Inventors: Bernhard Fischer, Vienna (AT); Rudolf Lucas, Aartselaar (BE)

(73) Assignee: Apeptico Forschung UND Entwicklung GMBH, Vienna (AT)

( * ) Notice: Subject to any disclaimer, the term of this patent is extended or adjusted under 35 U.S.C. 154(b) by 0 days.

(21) Appl. No.: 13/805,839

(22) PCT Filed: Oct. 20, 2010

(86) PCT No.: PCT/EP2010/006408
§ 371 (c)(1),
(2), (4) Date: Dec. 20, 2012

(87) PCT Pub. No.: WO2011/160664
PCT Pub. Date: Dec. 29, 2011

(65) Prior Publication Data
US 2013/0116200 A1    May 9, 2013

(30) Foreign Application Priority Data

Jun. 21, 2010 (EP) .................................... 10166637

(51) Int. Cl.
A61K 38/12    (2006.01)
C07K 7/64     (2006.01)
A61K 38/08    (2006.01)
C07K 14/525   (2006.01)

(52) U.S. Cl.
CPC .............. *C07K 14/525* (2013.01); *A61K 38/12* (2013.01)

(58) Field of Classification Search
None
See application file for complete search history.

(56) References Cited

U.S. PATENT DOCUMENTS

2003/0105021 A1*  6/2003  Lucas et al. .................. 514/13

FOREIGN PATENT DOCUMENTS

| EP | WO 00/09149    | * | 2/2000  | ........... A61K 38/19 |
| EP | 1264599 A1     |   | 12/2002 | |
| JP | 2012519188 A   |   | 8/2012  | |
| WO | 2006013183 A1  |   | 2/2006  | |
| WO | 2008148545 A1  |   | 12/2008 | |

OTHER PUBLICATIONS

Fowler, MJ. Clinical Diabetes. 26(2);77-82:2008.*
Armstrong et al. Arch Surg. 135;1405-1409:2000.*
Diuretics—loop diuretics. UMMC. http://umm.edu/health/medical/altmed/depletion/diuretics-loop-diuretics.*
Di Napoli, P., et al., "Trimetazidine improves post-ischemic recovery by preserving endothelial nitric oxide synthase expression in isolated working rat hearts," Nitro Oxide (2007) 16:228-236.
Elia, et al., "Functional Identification of the Alveolar Edema Reabsorption Activity of Murine Necrosis Factor-α," Am J Respir Crit Care Med (2003) 168:1043-1050.
Hribar, M., et al., "The lectin-like domain of tumor necrosis factor-α increases membrane conductance in microvascular endothelial cells and peritoneal macrophages," Eur. J. Immunol. (1999) 29:3105-3111.
Marquardt, A, et al., "Identification, affinity characterisation and biological interactions of lectin-like peptide-carbohydrate complexes derived from human TNF-α using high-resolution mass spectrometry," (2007) J. Pept. Sci. 13:803-810.
Romero, M.J., et al., "Diabetes-induced Coronary Vascular Dysfunction Involves Increased Arginase Activity," (2008) 102(1):95.
Romero, M. J., et al., "TNF-derived TIP peptide ameliorates High Glucose (HG)-induced Arginase (ARG) mediated Endothelial Dysfunction (ED) via inhibiting PKC-α activation," Faseb Journal (2010) 24:571.6.
Schalkwijk, C. G., et al., "Vascular complications in diabetes mellitus: the role of endothelial dysfunction," Clinical Science (2005) 109:143-159.
Xiong, C., et al., "The lectin-like domain of TNF protects from listeriolysis-induced hyperpermeability in human pulmonary microvascular endothelial cells—A crucial role for protein kinase C-α inhibition," Vascular Pharamacy (2010) 52:207-213.
Yang, G., et al., "Novel mechanisms of endothelial dysfunction in diabetes," J. Cardiovasc. Dis. Res. (2010) 1(2):59-63.
Woodman, et al., "Atrial natriuretic peptide prevents diabetes-induced endothelial dysfunction," Life Sciences (2008) 82:15-16 pp. 847-854.
European Search Report, 10166637.8, Sep. 30, 2010.
Office Action JP 2013-515709 Dated Dec. 16, 2014.
Ali, M. Irfan et al., "Deletion of Protein Tyrosine Phosphatase 1B Improves Peripheral Insulin Resistance and Vascular Function in Obese, Leptin Resistant Mice Via Reduced Oxidant Tone", Circ Res., Nov. 6, 2009, vol. 10, pp. 1013-1022.
Czikora, Istvan et al., "A novel tumor necrosis factor-medicated mechanism of direct epithelial sodium channel activation", American Journal of Respiratory and Critical Care Medicine, 2014, vol. 190, No. 5, pp. 522-532.
Belin de Chanteméle, Eric J. et al. "Obesity induced-insulin resistance causes endothelial dysfunction without reducing the vascular response to hindlimb ischemia", Basic Res Cardiol., Nov. 2009, vol. 104, No. 6, pp. 707-717.
Hay, Michael et al. "Clinical development success rates for investigational drugs", Nature Biotechnology, Jan. 2014, vol. 32, No. 1, pp. 40-51.

(Continued)

*Primary Examiner* — Amber D Steele
*Assistant Examiner* — Schuyler Milton
(74) *Attorney, Agent, or Firm* — Chainey P. Singleton; Edwin S. Flores; Chalker Flores, LLP (57) ABSTRACT

A peptide consisting of 7-17 amino acids and including the adjacent hexamer $TX_1EX_2X_3E$, where $X_1$, $X_2$ and $X_3$ can be any natural or non natural amino acid, wherein the peptide does not exhibit TNF-receptor-binding activity and is cyclic, for the treatment or prevention of vascular complications in diabetes patients.

11 Claims, 4 Drawing Sheets

(56) References Cited

OTHER PUBLICATIONS

Matthay, Michael A. et al. "Lung Epithelial Fluid Transport and the Resolution of Pulmonary Edema", Physiol Rev, 2002, vol. 82, pp. 569-600.

Bull, Marcia B. et al. "Amiloride: A Postassium-Sparing Natriuretic Agent" Circulation, Jan. 1968, vol. 37, pp. 45-53.

Romero, Maritza J. et al. "Diabetes-induced vascular dysfunction involves arginase I", Am J Physiol Heart Circ Physiol, 2012, vol. 302, pp. H159-H166.

* cited by examiner

SEQUENCE LISTING

```
<160> NUMBER OF SEQ ID NOS: 12

<210> SEQ ID NO 1
<211> LENGTH: 17
<212> TYPE: PRT
<213> ORGANISM: Artificial Sequence
<220> FEATURE:
<223> OTHER INFORMATION: synthetic peptide

<400> SEQUENCE: 1

Cys Gly Gln Arg Glu Thr Pro Glu Gly Ala Glu Ala Lys Pro Trp Tyr
1               5                   10                  15

Cys

<210> SEQ ID NO 2
<211> LENGTH: 20
<212> TYPE: PRT
<213> ORGANISM: Artificial Sequence
<220> FEATURE:
<223> OTHER INFORMATION: synthetic peptide

<400> SEQUENCE: 2

Lys Ser Pro Gly Gly Gln Arg Glu Thr Pro Glu Gly Ala Glu Ala Lys
1               5                   10                  15

Pro Trp Tyr Glu
            20

<210> SEQ ID NO 3
```

```
<211> LENGTH: 17
<212> TYPE: PRT
<213> ORGANISM: Artificial Sequence
<220> FEATURE:
<223> OTHER INFORMATION: synthetic peptide

<400> SEQUENCE: 3

Cys Gly Gln Arg Glu Ala Pro Ala Gly Ala Ala Ala Lys Pro Trp Tyr
1               5                   10                  15

Cys

<210> SEQ ID NO 4
<211> LENGTH: 6
<212> TYPE: PRT
<213> ORGANISM: Artificial Sequence
<220> FEATURE:
<223> OTHER INFORMATION: synthetic peptide

<400> SEQUENCE: 4

Thr Pro Glu Gly Ala Glu
1               5

<210> SEQ ID NO 5
<211> LENGTH: 14
<212> TYPE: PRT
<213> ORGANISM: Artificial Sequence
<220> FEATURE:
<223> OTHER INFORMATION: synthetic peptide

<400> SEQUENCE: 5

Gln Arg Glu Thr Pro Glu Gly Ala Glu Ala Lys Pro Trp Tyr
1               5                   10

<210> SEQ ID NO 6
<211> LENGTH: 14
<212> TYPE: PRT
<213> ORGANISM: Artificial Sequence
<220> FEATURE:
<223> OTHER INFORMATION: synthetic peptide

<400> SEQUENCE: 6

Pro Lys Asp Thr Pro Glu Gly Ala Glu Leu Lys Pro Trp Tyr
1               5                   10

<210> SEQ ID NO 7
<211> LENGTH: 17
<212> TYPE: PRT
<213> ORGANISM: Artificial Sequence
<220> FEATURE:
<223> OTHER INFORMATION: synthetic peptide

<400> SEQUENCE: 7

Cys Gly Pro Lys Asp Thr Pro Glu Gly Ala Glu Leu Lys Pro Trp Tyr
1               5                   10                  15

Cys

<210> SEQ ID NO 8
<211> LENGTH: 17
<212> TYPE: PRT
<213> ORGANISM: Artificial Sequence
<220> FEATURE:
<223> OTHER INFORMATION: synthetic peptide

<400> SEQUENCE: 8

Cys Gly Gln Lys Glu Thr Pro Glu Gly Ala Glu Ala Lys Pro Trp Tyr
1               5                   10                  15
```

-continued

```
Cys

<210> SEQ ID NO 9
<211> LENGTH: 17
<212> TYPE: PRT
<213> ORGANISM: Artificial Sequence
<220> FEATURE:
<223> OTHER INFORMATION: synthetic peptide

<400> SEQUENCE: 9

Cys Gly Gln Arg Glu Thr Pro Glu Gly Ala Glu Ala Arg Pro Trp Tyr
1               5                   10                  15

Cys

<210> SEQ ID NO 10
<211> LENGTH: 15
<212> TYPE: PRT
<213> ORGANISM: Artificial Sequence
<220> FEATURE:
<223> OTHER INFORMATION: synthetic peptide

<400> SEQUENCE: 10

Cys Gly Gln Arg Glu Thr Pro Glu Gly Ala Glu Ala Lys Pro Cys
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: synthetic peptide

<400> SEQUENCE: 11

Cys Gln Arg Glu Thr Pro Glu Gly Ala Glu Ala Lys Pro Trp Tyr Cys
1               5                   10                  15

<210> SEQ ID NO 12
<211> LENGTH: 17
<212> TYPE: PRT
<213> ORGANISM: Artificial Sequence
<220> FEATURE:
<223> OTHER INFORMATION: synthetic peptide

<400> SEQUENCE: 12

Cys Gly Gln Arg Glu Thr Pro Glu Gly Ala Glu Ala Lys Phe Trp Tyr
1               5                   10                  15

Cys
```

TREATMENT OF VASCULAR COMPLICATIONS OF DIABETES

CROSS-REFERENCE TO RELATED APPLICATIONS

This application is the National Stage of International Application No. PCT/EP2010/006408, filed on 20 Oct. 2010 claiming the priority of EP 10166637.8, filed on 21 Jun. 2010, the content of each of which is incorporated by reference herein.

The present invention relates to methods for prevention and treatment of vascular complications of diabetes.

Diabetes mellitus is a common metabolic disease worldwide affecting approx. 150 million people in 2000, which is predicted to rise to 220 million in 2010. Diabetes and its associated complications have become a public health problem of considerable magnitude. Cardiovascular disease causes most of the excess morbidity and mortality in diabetes mellitus. Adults with diabetes are at a 2- to 4-fold increased risk of cardiovascular events relative to those without diabetes. Cardiovascular disease accounts for up to 80% of premature excess mortality in diabetic patients. Because of the huge premature morbidity and mortality associated with this disease, prevention of its complications is a key issue.

In diabetes, dysfunction of the vascular endothelium is regarded as an important factor in the pathogenesis of diabetic micro- and macro-angiopathy. There are three main sources contributing to endothelial dysfunction in diabetes: i) hyperglycemia and its immediate biochemical sequelae directly alter endothelial function; ii) high glucose, which influences endothelial cell functioning indirectly by the synthesis of growth factors and vasoactive agents in other cells and alters endothelial monolayer permeability; iii) the components of the metabolic syndrome which can affect endothelial (Schalkwijk et al., Clin. Sci. 109 (2005), 143-159).

It is an object of the present invention to provide means for reducing the pathological impact of vascular complications in diabetes patients.

Accordingly, the present invention provides a peptide, consisting of 7-17 amino acids and including the adjacent hexamer $TX_1EX_2X_3E$, wherein $X_1$, $X_2$ and $X_3$ can be any natural or non natural amino acid, wherein the peptide does not exhibit TNF-specific inflammatory activity (Hribar et al., Eur. J. Immunol. 1999; Elia et al., AJRCCM 2003; see also: example section) and is cyclic for the treatment and prevention of vascular complications in diabetes patients.

$X_1$, $X_2$ and $X_3$ are preferably chosen from the 20 natural standard amino acids of the basic set of amino acids for natural protein synthesis; even more preferred $X_1$, $X_2$ and $X_3$ are chosen from the natural amino acids with hydrophobic side chain (Ala, Ile, Leu, Met, Val, Pro and Gly). Specifically preferred are (independently from each other) $X_1$=Pro; $X_2$ and $X_3$=Gly, Ala, Val, Leu or Ile; $X_2X_3$ being preferably a dipeptide chosen from Gly-Ala, Gly-Val, Ala-Gly or Ala-Val.

Preferably, the peptide according to present invention consists of 7-17 amino acids and contains the hexamer TPEGAE (SEQ ID No. 4), wherein the peptide is cyclic and has no TNF-receptor-binding activity.

A particularly preferred embodiment of the present invention relates to a cyclic peptide, consisting of a sequence of consecutive amino acids selected from the group

QRETPEGAEAKPWY (SEQ ID NO. 5)

PKDTPEGAELKPWY (SEQ ID NO. 6)

CGQRETPEGAEAKPWYC (SEQ ID NO. 1)
and

CGPKDTPEGAELKPWYC (SEQ ID NO. 7)

and fragments of at least seven amino acids containing the hexamer TPEGAE for the treatment and prevention of vascular complications in diabetes patients.

The peptides according to the present invention are known for example from European Patent EP 1 264 599 B1 for use in the treatment of pulmonary oedema.

Surprisingly, these peptides have turned out to be specifically beneficial for the treatment and prevention of vascular complications in diabetes patients. The present invention therefore concerns the use of these peptides for the manufacture of a medicament for the treatment and prevention of vascular complications in diabetes patients.

The type of diabetes to be treated or prevented according to the present invention can be any kind of common diabetes, preferably Type 1 diabetes, Type 2 diabetes, gestational diabetes, congenital diabetes, cystic fibrosis-related diabetes, steroid diabetes (induced by high doses of glucocorticoids), and several forms of monogenic diabetes; however, Type I and Type II being the preferred target diseases for the present invention, especially Type II diabetes. The present invention provides a method for the treatment and prevention of vascular complications in diabetes patients wherein an effective amount of a peptide according to the present invention (or a mixture of such peptides) is administered to a diabetes patient having or being at risk of developing a vascular complication as described herein.

Diabetes is characterized by recurrent or persistent hyperglycemia, and is diagnosed by demonstrating any one of the following:

Fasting plasma glucose level at or above 7.0 mmol/L (126 mg/dL (according to the current (WHO) definition, two fasting glucose measurements above 126 mg/dL (7.0 mmol/L) is considered diagnostic for diabetes mellitus)

Plasma glucose at or above 11.1 mmol/L (200 mg/dL) two hours after a 75 g oral glucose load as in a glucose tolerance test Symptoms of hyperglycemia and casual plasma glucose at or above 11.1 mmol/L (200 mg/dL)

Glycated hemoglobin (hemoglobin A1C) at or above 6.5 (This criterion was recommended by the American Diabetes Association in 2010; it has yet to be adopted by the WHO)

Patients with fasting glucose levels from 100 to 125 mg/dL (5.6 to 6.9 mmol/L) are considered to have impaired fasting glucose. Patients with plasma glucose at or above 140 mg/dL (7.8 mmol/L), but not over 200 mg/dL (11.1 mmol/L), two hours after a 75 g oral glucose load are considered to have impaired glucose tolerance. Of these two pre-diabetic states, the latter in particular is a major risk factor for progression to full-blown diabetes mellitus as well as cardiovascular disease (as a major vascular complication in diabetes patients).

Vascular complications in diabetes patients can be caused by micro- and macroangiopathy. Retinal and renal microangiopathy cause diabetic retinopathy and nephropathy, respectively, and microangiopathy of the vasa nervorum is important in the pathogenesis of neuropathy. Macroangiopathy in diabetes consists mainly of an accelerated form of atherosclerosis and affects the coronary, carotid and peripheral arteries, thus increasing the risk of myocardial infarction, stroke and diabetic foot disease. Large clinical trials in both Type I and Type II diabetes have demonstrated that hyperglycaemia plays an important role in the pathogenesis of microvascular complications, such as microvascular cardiac hyperpermeability. Hypertension, smoking, hypercholesterolaemia, dyslipidaemia, obesity and hyperhomocysteinaemia are additional major causes of microangiopathy.

Risk of macroangiopathy does not appear to be strongly related to hyperglycaemia, but is related to general risk factors for atherothrombosis, such as age, smoking, hypertension, hypercholesterolaemia, dyslipidaemia, obesity and hyperhomocysteinaemia. All of the above-mentioned factors create a state of constant and progressive damage to the vascular wall, manifested by a low-grade inflammatory process and endothelial dysfunction. As already stated above (Schalkwijk et al., 2005) dysfunction of the vascular endothelium is regarded as an important factor in the pathogenesis of micro- and macroangiopathy. Parameters involved in vascular complications during diabetes are a dysfunctional vasorelaxation capacity and a cardiac hyperpermeability.

The present invention is therefore specifically suitable in the prevention or treatment of micro- and macroangiopathy, myocardial infarction, microvascular cardiac hyperpermeability, stroke, neuropathy, retinopathy, nephropathy or diabetic foot disease in diabetic patients.

With the present invention, the vascular complications of diabetes patients can be treated or prevented. Since diabetes is currently a disease which cannot be finally cured, the "treatment" according to the present invention has to be understood as including the provision of an amelioration of the vascular complications of diabetes patients compared to the usual progression of these complications. Similarly, the "prevention" according to the present invention also includes that the vascular complications of diabetes patients are occurring later in the disease state by provision of the present invention compared to the usual occurrence of these complications in diabetes patients.

A particularly preferred peptide according to the present invention consists of the amino acid sequence CGQRETPEGAEAKPWYC and is circularized via the C residues (at position 1 and 17).

The cyclization according to the present invention may be obtained via direct intramolecular cyclization of functional groups of the amino acid residues, preferably via C—C link (through a disulfide bond between the two C residues). The peptide may also be coupled (e.g. via two cysteines) to a carrier substance. Preferably, the peptides according to the present invention therefore exhibit cysteine residues at the beginning and end of the molecule. Other functional groups capable of cyclization of the peptide can be used, eg by an amine or alcohol group of an amino acid residue leading to an amide or ester ring closure (this may include for example the amino acids aspartic acid and glutamic acid with serine, threonine, tyrosine, asparagine, glutamine or lysine, which may preferably be cyclized intramolecularly). Other preferred inventive peptides are, therefore, for example CGQKETPEGAEAKPWYC (SEQ ID NO. 8), CGQRETPEGAEARPWYC (SEQ ID NO. 9), CGQRETPEGAEAKPC (SEQ ID NO. 10), CQRETPEGAEAKPWYC (SEQ ID NO. 11) or CGQRETPEGAEAKFWYC (SEQ ID NO. 12).

Suitable carriers are all commonly used pharmaceutical carrier substances which exhibit suitable binding groups to the peptides according to the present invention, eg carriers which react with the SH-groups of the cysteines to enter into a covalent bond. Other suitable carriers comprise adjacent bifunctional groups (eg. an acid group in vicinity to an amine or alcohol group). In this context it is important to note that "cyclization" according to the present invention includes both, the intramolecular cyclization and the involvement of a carrier (from which the bound peptide protrudes (wherein the N- and the C-terminus of the peptide is bound to the carrier to form a loop on the carrier)). In both embodiments, the cyclic peptide shows the cyclic spatial structure and is stabilized accordingly. In some embodiments, the intramolecular cyclization is preferred, especially if the lack of a carrier molecule is advantageous due to solubility reasons or due to reasons of molecular weight or molecule size.

According to another aspect, the present invention relates to a pharmaceutical composition containing the peptide according to the present invention (or a mixture of peptides according to the present invention) and a pharmaceutical carrier. This pharmaceutical composition is used for the treatment or prevention for vascular complications in diabetes patients.

The term "pharmaceutical composition" refers to any composition or preparation that contains a peptide, as defined above, which ameliorates, cures or prevents the conditions described herein. In particular, the expression "a pharmaceutical composition" refers to a composition comprising a peptide according to the present invention and a pharmaceutically acceptable carrier or excipient (both terms are used interchangeably). Suitable carriers or excipients are known to the person skilled in the art, for example saline, Ringer's solution, dextrose solution, buffers, Hank solution, vesicle forming compounds (e.g. lipids), fixed oils, ethyl oleate, 5% dextrose in saline, substances that enhance isotonicity and chemical stability, buffers and preservatives. Other suitable carriers include any carrier that does not itself induce the production of antibodies in the patient that are harmful for the patient. Examples are well tolerable proteins, polysaccharides, polylactic acids, polyglycolic acid, polymeric amino acids and amino acid copolymers. As already described above, the peptides according to the present invention can be cyclized to such a carrier by direct covalent bond. This pharmaceutical composition can (as a drug) be administered via appropriate procedures known to the skilled person. The preferred route of administration is parenteral administration, in particular through inhalation (aerosol) or intravenous administration. For parenteral administration, the pharmaceutical composition of the present invention is provided in injectable dosage unit form, eg as a solution, suspension or emulsion, formulated in conjunction with the above-defined pharmaceutically acceptable excipients. The dosage and method of administration, however, depends on the individual patient to be treated. In general, the peptide according to the present invention is administered at a dose of between 1 µg/kg and 10 mg/kg, more preferably between 10 µg/kg and 5 mg/kg, most preferably between 0.1 and 2 mg/kg. Preferably, the composition will be administered as an intraperitoneal bolus dosage. Also continuous infusion can be applied. In this case, the peptide is delivered at a dose of 5 to 20 µg/kg/minute, more preferably 7-15 µg/kg/minute infusion. According to the present invention a particularly preferred peptide according to the present invention (also referred to as "AP 301") has the following amino acid sequence:

SEQ ID NO: 1
(NH$_2$) Cys-Gly-Gln-Arg-Glu-Thr-Pro-Glu-Gly-Ala-Glu-Ala-Lys-Pro-Trp-Tyr-Cys (COOH).

The invention is further described by the following examples and the drawing figures, yet without being limited thereto.

EXAMPLES

1. Effect of the TNF-Derived TIP Peptide on Endothelial Relaxation During Streptozocin-Induced Diabetes in Rats Streptozocin (STZ) is an antibiotic that can cause pancreatic β-cell destruction, so it is widely used experimentally as an agent capable of inducing insulin-dependent diabetes mellitus (IDDM), also known as type 1 diabetes mellitus (T1DM).

Figure 1:
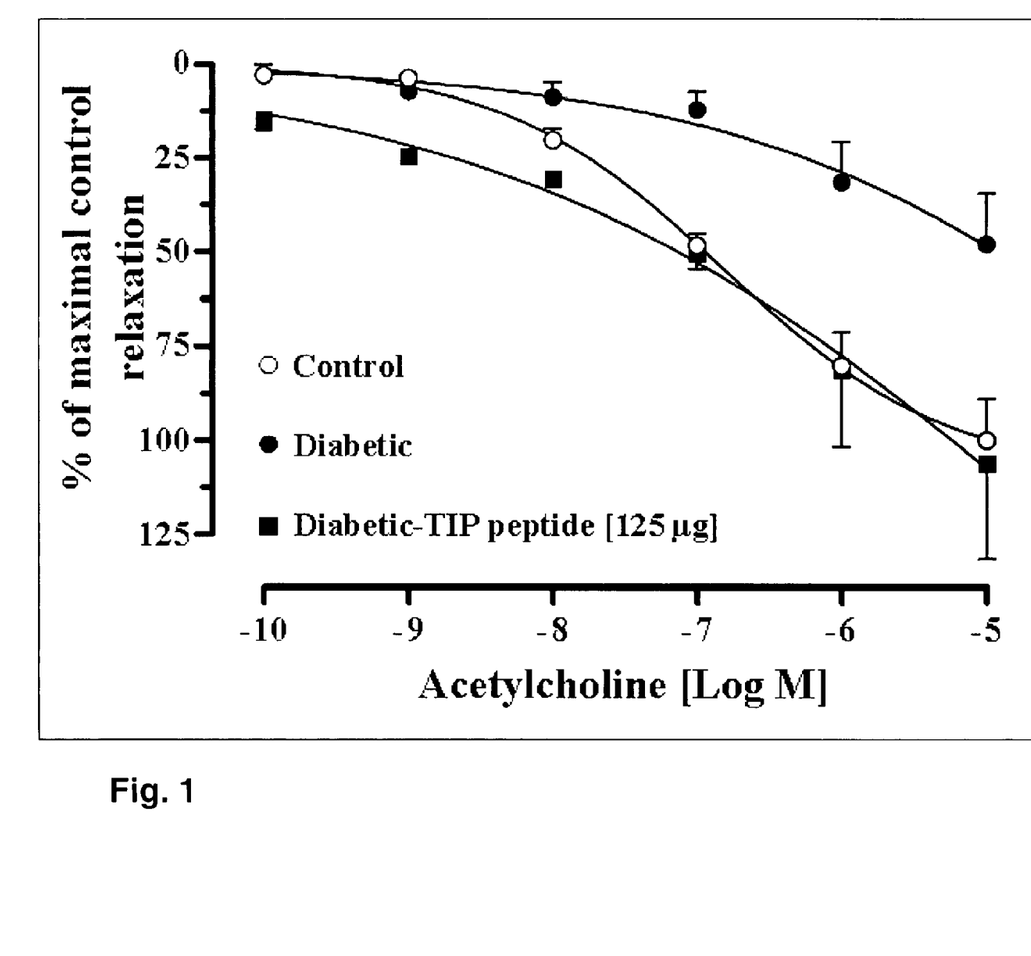
FIG. 1 shows the acetylcholine-induced vasorelaxation in U46619-contracted septal coronary arteries from control, Streptozocin (STZ)-treated or TIP peptide+STZ treated rats, 4 wks after STZ injection (n=3)

In this experiment, Male Sprague-Dawley rats (240 to 265 g, n=3) were divided into three groups: 1. Control rats receiving injections of vehicle alone, 2. rats rendered diabetic with STZ (50 mg/kg, intraperitoneally) and 3. STZ-treated rats co-treated with TIP peptide (125 μg, i.p.) every three days, starting two days prior to STZ injection, for four weeks. Rats with blood levels >350 mg/dL were considered to be diabetic. Septal coronary arteries from rats were prepared as previously described (Romero et al., 2008). Briefly, vascular coronary artery segments were mounted in a small vessel myograph (Danish Myo Technology), contracted with the thromboxane A2 analog U46619 9,11-Dideoxy-9a,11a-methanoepoxy prostaglandin F2a
Chemical Name: (5Z)-7-[(1R,4S,5S,6R)-6-[(1E,3S)-3-Hydroxy-1-octenyl]-2-oxabicyclo[2.2.1]hept-5-yl]-5-heptenoic acid
and tested for their ability to relax in response to progressive concentrations of acetylcholine. The vasorelaxant responses are expressed as percent of maximal control relaxation. As shown in FIG. 1, septal coronary arteries isolated from STZ-induced diabetic rats displayed a significantly reduced vasorelaxation capacity, as compared to control rats. Co-treatment of the diabetic rats with the TNF-derived TIP peptide AP301 significantly improved the vasorelaxation response in the septal coronary arteries. This acknowledged diabetes animal model shows that the TNF-derived TIP peptide AP301 can improve endothelial vasorelaxation during diabetes.

Figure 2:
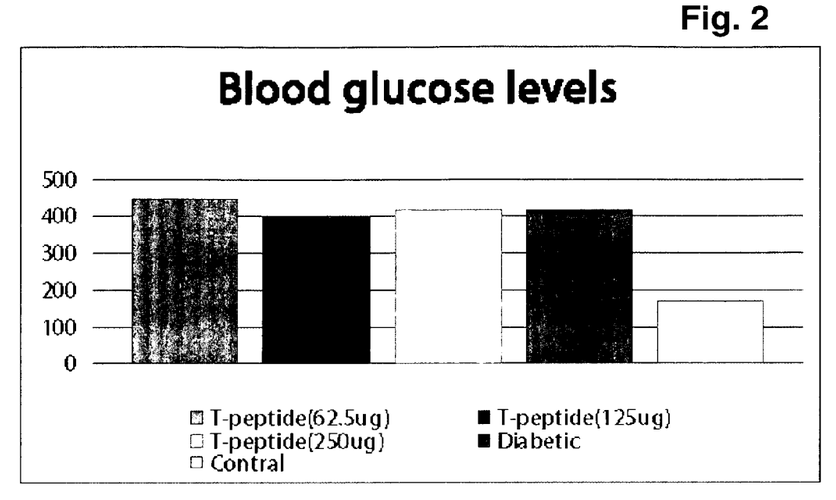
FIG. 2 shows that TIP peptide treatment does not affect blood glucose levels in STZ-treated rats (n=3)
Figure 3:
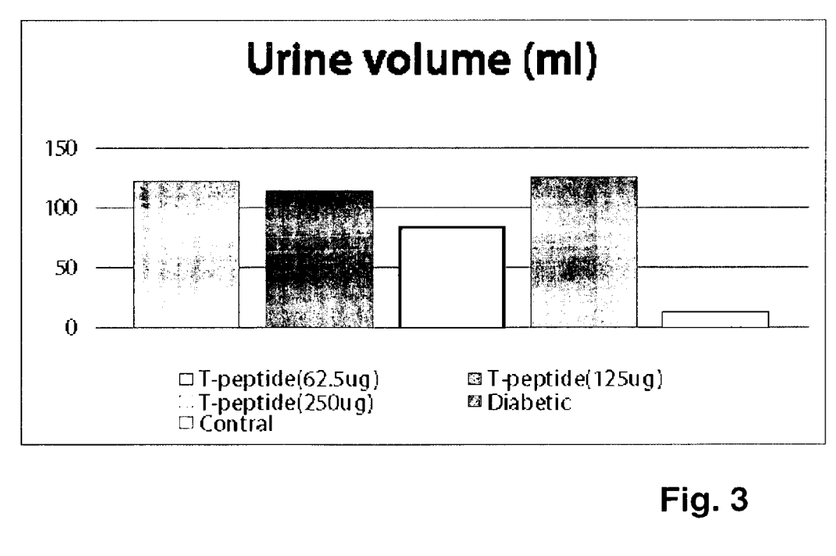
FIG. 3 shows that TIP peptide treatment slightly and dose-dependently decreases urine volume in STZ-treated rats (n=3)

The effect of the TIP peptide treatment according to the present invention in these rats on blood glucose levels, blood pressure urine volume and weight was also investigated (FIGS. 2 and 3). The TIP peptide-treated animals had comparable glucose levels as the STZ group, but had a lower urine volume and a higher blood pressure than the STZ group. They also displayed increased weight loss. The TIP peptide according to the present invention also inhibits STZ-associated cardiac permeability in vivo.

Figure 4:
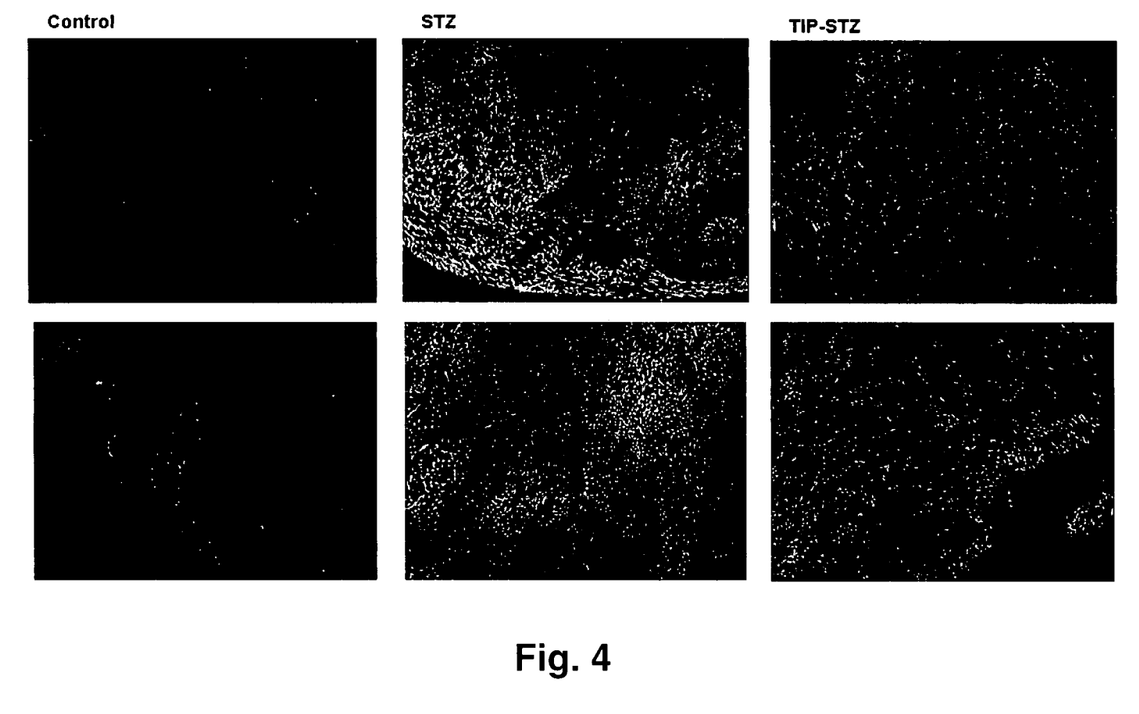
FIG. 4 shows fluorescence microscopy images of perfused rat hearts (Langendorff) with FITC-BSA.
Figure 5:
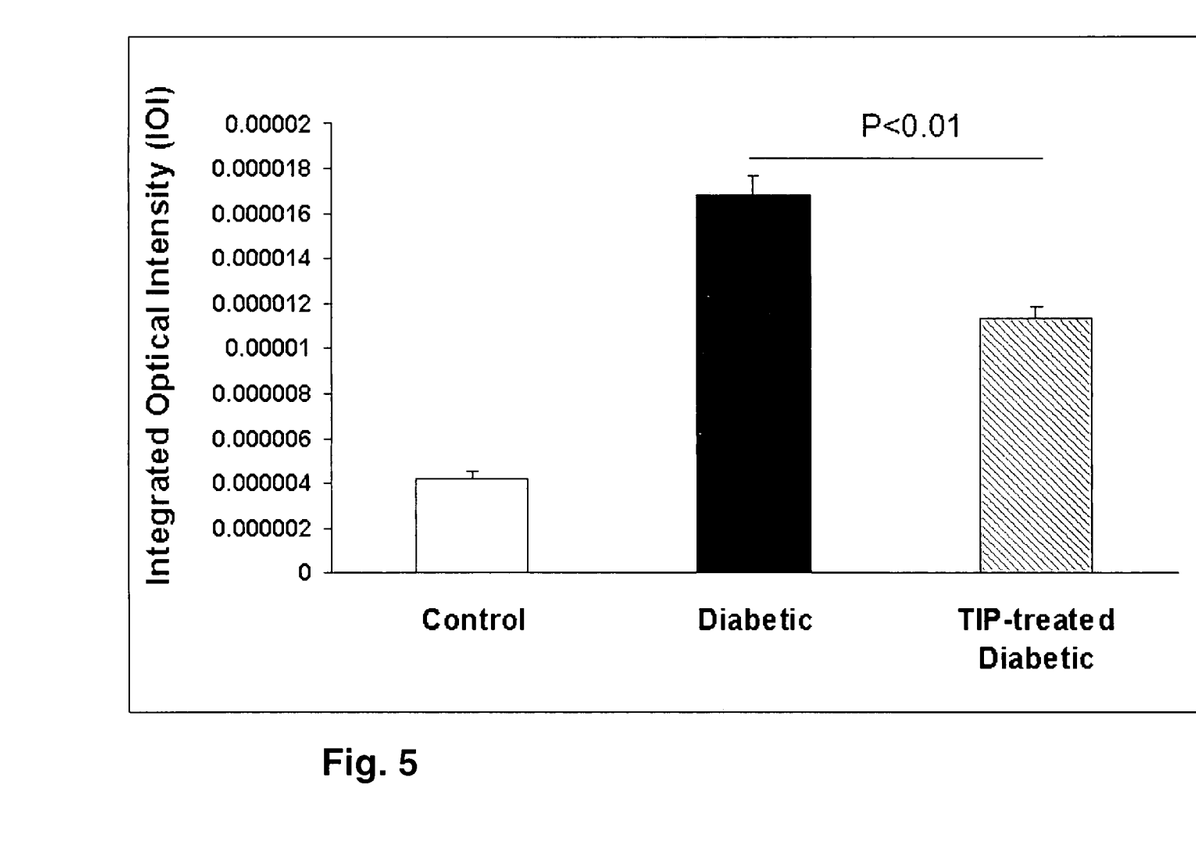
FIG. 5 shows the effect of TIP peptide (125 μg/rat over 4 wks i.p.) on cardiac permeability (assessed by Albumin-FITC incorporation using the Langendorff method).

Following the same protocol as above, hearts from Ctrl, STZ-treated and TIP/STZ treated rats were isolated after 4 wks. The hearts were perfused using the Langendorff method with BSA-FITC (Di Napoli et al., Nitric Oxide 16 (2007), 228-236). Hearts were subsequently frozen in liquid nitrogen and slices were cut with a microtome. Subsequently, fluorescence was assessed in 4 slices of each heart and cumulative fluorescence responses were recorded. As shown in FIGS. 4 and 5, TIP peptide AP301 significantly inhibits cardiac hyperpermeability: Fluorescence microscopy of ventricles from FITC-albumin-perfused rat hearts detected significant less fluorescence dye in the presence of TIP peptide (FIG. 5) compared to experiments without TIP peptide (FIG. 4).

With the present animal model it could be shown that STZ-induced Type I Diabetes in rats causes vascular dysfunction, as characterized by impaired endothelial-dependent vasorelaxation and hyperpermeability in the heart.

The data provided with the present animal model show that treatment with a representative member of the peptides according to the present invention (the "TIP peptide"; "AP301"; SEQ ID No. 1) could efficiently treat and prevent diabetic vascular complications in these animals. These data support that treatment with the peptides according to the present invention is a promising approach for new therapies for the treatment of diabetic vascular complications also in human patients.

2. Ex vivo Assessment of Pro-Inflammatory Properties of the AP301 Peptide in Human Whole Blood An ex vivo safety pharmacological study of the AP301 peptide in human whole blood was performed to assess whether the AP301 peptide results in the release of the pro-inflammatory marker interleukin-6 (IL-6) from fresh human whole blood (i.e. whether APN 301 exhibits TNF-specific inflammatory activity).

In this study, fresh human whole blood has been used, as it represents a predictive model system for the assessment of inflammatory response in vivo.

Summary of Methodology

It was the goal of this study to determine the pro-inflammatory signalling capacity of the AP301 peptide. Whole blood cultures were used and the secretion of interleukin-6 (IL-6), a very sensitive marker for pro-inflammatory stimulation, was quantified by ELISA.

Test System
  Test system 25 ml of freshly taken heparinized blood from 5 healthy volunteers (HV) was used in the assays.
Test Item
  Identification AP301 peptide (dose: 1 ng/ml to 10 μg/ml; single administration in solution)
  Description White powder, purity 96%
Whole Blood Cultures
  Whole blood (WB) cultures were done by pipetting 1 ml of WB into wells of 24 well plates. In each experiment unstimulated and control-stimulated cultures were included.
  If possible the substances and stimulants to be investigated were always added in an identical volume to each well of a given experiment, not greater than 10% of the total volume contained in a well. Unstimulated controls received PBS. Volume adjustments and dilutions for different treatments were also done with PBS.
  The content of each well was mixed and the plates incubated at 37° C. and 5% $CO_2$ for 24 hours. After incubation the content of each well was transferred to a fresh 1.5 ml microtube and centrifuged at 8000-9000×g for 15 minutes. The supernatant of each sample was transferred individually to two 1.5 ml microtubes and kept at −20° C. until use.

Detection of Interleukin-6

Interleukin-6 was quantified by a specific ELISA (Human IL-6 ELISA Set, BD Biosciences, Cat. No. 555220) employing an anti-human IL-6 antibody as capture antibody, a biotinylated anti-human IL-6 detection antibody, avidin-horseradish peroxidase conjugate as enzyme reagent, and recombinant IL-6 as standard. Absorbance measurement was performed at 450 nm using the Packard FusionReader.

Data Analysis

The results for each plate were stored and evaluated using the FusionDataAnalysis software.

Summary of Study Results

It was the goal of this study to determine the pro-inflammatory signalling capacity of the AP301 peptide. Whole blood cultures were used and the secretion of IL 6, a very sensitive marker for pro inflammatory stimulation, was quantified by ELISA.

Whole blood samples from five healthy volunteers were either left unstimulated (negative control), stimulated with high and low doses of LPS (positive controls), or incubated with peptide in nine semi-logarithmic dilutions ranging from 10 µg/ml to 1 ng/ml.

TABLE

Release of Interleukin-6 from fresh human whole blood upon addition of peptide AP301 and LPS

| Concentration | AP301 peptide | Positive control (LPS) |
|---|---|---|
| | Concentration of IL-6 (pg/ml, n = 5) | |
| 0 (negative control) | less than 0.5 | less than 0.5 |
| 10 mg/ml | less than 0.5 | 195.640 |
| 1 mg/ml | less than 0.5 | 108.370 |
| 3 ng/ml | less than 0.5 | 34.867 |
| 1 ng/ml | less than 0.5 | not determined |

The results clearly reveal that the AP301 peptide did not induce any detectable level of IL-6 secretion at any of the concentrations tested. The positive controls (LPS) resulted in a strong induction of IL 6 secretion.

DISCUSSION

The experiments have been performed to assess whether the AP301 peptide mediates the induction of a pro-inflammatory response. Readout parameter was the induced secretion of IL-6 in whole blood cultures from five healthy donors. The results clearly showed that the AP301 peptide did not induce any detectable level of IL-6 in any donor's cultures. Therefore it is demonstrated that the AP301 peptide did not induce a pro-inflammatory response in the chosen ex vivo model.

The invention claimed is:

1. A method for the treatment of vascular complications, except retinopathy, in diabetes patients comprising the step of:
administering to a diabetes patient, said diabetes patient being at risk of developing vascular complications, except retinopathy, or having vascular complications, except retinopathy,
an amount of a peptide consisting of 7-17 amino acids and including the hexamer $TX_1EX_2X_3E$, wherein $X_1$, $X_2$ and $X_3$ can be any natural or non natural amino acid, wherein the peptide does not exhibit TNF-receptor-binding activity and is cyclic, for treatment of vascular complications, except retinopathy, in said patient.

2. A method for the treatment of vascular complications, except retinopathy, in diabetes patients comprising the step of:
administering to a diabetes patient, said diabetes patient being at risk of developing vascular complications, except retinopathy, or having vascular complications, except retinopathy,
an amount of a peptide consisting of 7-17 amino acids and including the hexamer TPEGAE of SEQ ID NO: 4, wherein the peptide does not exhibit TNF-receptor-binding activity and is cyclic, for treatment of vascular complications, except retinopathy, in said patient.

3. A method for the treatment of vascular complications, except retinopathy, in diabetes patients comprising the step of:
administering to a diabetes patient, said diabetes patient being at risk of developing vascular complications, except retinopathy, or having vascular complications, except retinopathy;

an amount of a cyclic peptide consisting of a sequence of consecutive amino acids selected from the group consisting of

QRETPEGAEAKPWY, SEQ ID NO: 5

PKDTPEGAELKPWY, SEQ ID NO: 6

CGQRETPEGAEAKPWYC, SEQ ID NO: 1

CGPKDTPEGAELKPWYC SEQ ID NO: 7
and fragments of at least seven amino acids containing the hexamer TPEGAE of SEQ ID NO: 4, for treatment of vascular complications, except retinopathy, in said patient.

4. The method of claim 1 for the treatment of micro- and macroangiopathy, myocardial infarction, microvascular cardiac hyperpermeability, stroke, neuropathy, nephropathy or diabetic foot disease in said patient.

5. The method of claim 1, characterized in that the peptide has the amino acid sequence CGQRETPEGAEAKPWYC of SEQ ID NO: 1 and cyclized via the C-residues.

6. The method according to claim 5, characterized in that the peptide is cyclized by a disulfide bond between the C-residues.

7. A method for the treatment of vascular complications, except retinopathy, in diabetes patients comprising the step of:
    administering to a diabetes patient, said diabetes patient being at risk of developing vascular complications, except retinopathy, or having vascular complications, except retinopathy,
    an amount of a pharmaceutical composition comprising a peptide consisting of 7-17 amino acids and including the hexamer $TX_1EX_2X_3E$, wherein $X_1$, $X_2$ and $X_3$ can be any natural or non natural amino acid, wherein the peptide does not exhibit TNF-receptor-binding activity and is cyclic, and a pharmaceutical carrier, for treatment of vascular complications, except retinopathy, in said patient.

8. The method of claim 7, characterized in that the peptide has the amino acid sequence is CGQRETPEGAEAKPWYC of SEQ ID NO: 1 and is cyclized via the C-residues.

9. The method of claim 2 for the treatment of micro- and macroangiopathy, myocardial infarction, microvascular cardiac hyperpermeability, stroke, neuropathy, nephropathy or diabetic foot disease in said patient.

10. The method of claim 2, characterized in that the peptide has the amino acid sequence CGQRETPEGAEAKPWYC of SEQ ID NO: 1 and cyclized via the C-residues.

11. The method of claim 10, characterized in that the peptide is cyclized by a disulfide bond between the C-residues.

\* \* \* \* \*